(12) United States Patent
Zhuang et al.

(10) Patent No.: US 9,486,162 B2
(45) Date of Patent: Nov. 8, 2016

(54) SPATIAL NEEDLE GUIDANCE SYSTEM AND ASSOCIATED METHODS

(75) Inventors: Bo Zhuang, Richmond (CA); Laurent Pelissier, North Vancouver (CA); Alex Antonio, Burnaby (CA)

(73) Assignee: Ultrasonix Medical Corporation (CA)

( * ) Notice: Subject to any disclaimer, the term of this patent is extended or adjusted under 35 U.S.C. 154(b) by 1347 days.

(21) Appl. No.: 12/986,804

(22) Filed: Jan. 7, 2011

(65) Prior Publication Data

US 2012/0016316 A1    Jan. 19, 2012

Related U.S. Application Data

(60) Provisional application No. 61/393,788, filed on Oct. 15, 2010, provisional application No. 61/293,546, filed on Jan. 8, 2010.

(51) Int. Cl.
*A61B 5/15*  (2006.01)
*A61B 5/153*  (2006.01)
(Continued)

(52) U.S. Cl.
CPC ......... *A61B 5/1422* (2013.01); *A61B 5/15003* (2013.01); *A61B 5/1535* (2013.01); *A61B 5/150404* (2013.01); *A61B 5/150519* (2013.01); *A61B 5/150572* (2013.01); *A61B 5/150748* (2013.01); *A61B 10/0233* (2013.01); *A61B 17/3403* (2013.01); *A61B 17/3415* (2013.01); *A61B 17/3468* (2013.01); *A61B 34/20* (2016.02); *A61B 5/062* (2013.01); *A61B 5/6849* (2013.01); *A61B 8/0841* (2013.01);
(Continued)

(58) Field of Classification Search
CPC ...... A61B 18/18; A61B 5/05; A61B 5/1422; A61B 5/150519; A61B 5/150404
USPC ................................ 600/407, 431–435, 439
See application file for complete search history.

(56) References Cited

U.S. PATENT DOCUMENTS 4,173,228 A    11/1979    Van Steenwyk et al.
4,567,896 A    2/1986    Barnea et al.
(Continued)

FOREIGN PATENT DOCUMENTS

EP    1076512 A1    11/1999
WO    9424933 A1    11/1994
(Continued)

OTHER PUBLICATIONS

Hsu, P-W et al., "Freehand 3D Ultrasound Calibration: A Review", CUED/F-INFENG/TR 584, University of Cambridge Department of Engineering, Dec. 2007.

*Primary Examiner* — Peter Luong
(74) *Attorney, Agent, or Firm* — Anthony M. Del Zoppo, III; Driggs, Hogg, Daugherty & Del Zoppo, Co., LPA

(57) ABSTRACT

Methods and apparatus for positioning a elongate hollow member at a desired location in a body in a medical procedure are provided. A position marker is removably disposed within a sheath. The sheath may be disposable. The sheath and enclosed position marker may be inserted into a lumen of a member to be positioned. The position in space of the position marker may be monitored by a position sensor to provide real-time information regarding a position of the member. The spatial relationship between the position marker and member may be fixed by securing the mounting member to the sheath and securing the sheath to the member.

21 Claims, 12 Drawing Sheets

(51) Int. Cl.
*A61B 10/02* (2006.01)
*A61B 17/34* (2006.01)
*A61B 5/06* (2006.01)
*A61B 5/00* (2006.01)
*A61B 8/08* (2006.01)
*A61B 8/00* (2006.01)
*A61B 17/00* (2006.01)
*A61M 5/42* (2006.01)

(52) U.S. Cl.
CPC ......... *A61B 8/4254* (2013.01); *A61B 17/3498* (2013.01); *A61B 2017/00469* (2013.01); *A61B 2017/347* (2013.01); *A61B 2017/3413* (2013.01); *A61B 2034/2051* (2016.02); *A61B 2034/2055* (2016.02); *A61B 2090/378* (2016.02); *A61B 2090/3937* (2016.02); *A61B 2090/3975* (2016.02); *A61M 5/427* (2013.01)

(56) References Cited

U.S. PATENT DOCUMENTS

| | | | |
|---|---|---|---|
| 4,905,698 A | 3/1990 | Strohl, Jr. et al. | |
| 5,078,140 A | 1/1992 | Kwoh | |
| 5,095,910 A | 3/1992 | Powers | |
| 5,161,536 A | 11/1992 | Vilkomerson et al. | |
| 5,195,526 A * | 3/1993 | Michelson | 600/431 |
| 5,211,165 A | 5/1993 | Dumoulin et al. | |
| 5,379,779 A * | 1/1995 | Rowland et al. | 600/585 |
| 5,425,367 A | 6/1995 | Shapiro et al. | |
| 5,443,489 A | 8/1995 | Ben-Haim | |
| 5,515,853 A | 5/1996 | Smith et al. | |
| 5,638,819 A | 6/1997 | Manwaring et al. | |
| 5,647,373 A | 7/1997 | Paltieli | |
| 5,738,632 A * | 4/1998 | Karasawa | 600/410 |
| 5,797,849 A | 8/1998 | Vesely et al. | |
| 5,868,675 A | 2/1999 | Henrion et al. | |
| 5,879,357 A * | 3/1999 | Heaton et al. | 606/116 |
| 6,216,029 B1 | 4/2001 | Paltieli | |
| 6,246,898 B1 | 6/2001 | Vesely et al. | |
| 6,317,616 B1 | 11/2001 | Glossop | |
| 6,524,247 B2 | 2/2003 | Zhao et al. | |
| 6,574,497 B1 * | 6/2003 | Pacetti | 600/420 |
| 6,628,977 B2 | 9/2003 | Graumann et al. | |
| 6,733,458 B1 | 5/2004 | Steins et al. | |
| 6,764,449 B2 | 7/2004 | Lee et al. | |
| 6,785,571 B2 | 8/2004 | Glossop | |
| 6,875,179 B2 | 4/2005 | Ferguson et al. | |
| 6,920,347 B2 | 7/2005 | Simon et al. | |
| 7,142,905 B2 | 11/2006 | Slayton et al. | |
| 7,174,202 B2 | 2/2007 | Bladen et al. | |
| 7,221,972 B2 | 5/2007 | Jackson et al. | |
| 7,244,234 B2 | 7/2007 | Ridley et al. | |
| 7,366,562 B2 | 4/2008 | Dukesherer et al. | |
| 7,529,393 B2 | 5/2009 | Peszynski et al. | |
| RE40,852 E | 7/2009 | Martinelli et al. | |
| 7,599,730 B2 | 10/2009 | Hunter et al. | |
| RE41,066 E | 12/2009 | Martinelli et al. | |
| 2002/0188196 A1 * | 12/2002 | Burbank et al. | 600/431 |
| 2004/0097806 A1 | 5/2004 | Hunter et al. | |
| 2004/0267121 A1 | 12/2004 | Sarvazyan et al. | |
| 2005/0085793 A1 | 4/2005 | Glossop | |
| 2005/0182295 A1 | 8/2005 | Soper et al. | |
| 2006/0009714 A1 * | 1/2006 | Higaki et al. | 600/576 |
| 2006/0184016 A1 | 8/2006 | Glossop | |
| 2006/0241577 A1 | 10/2006 | Balbierz et al. | |
| 2007/0167787 A1 | 7/2007 | Glossop et al. | |
| 2007/0232882 A1 | 10/2007 | Glossop et al. | |
| 2008/0132911 A1 | 6/2008 | Sobe | |
| 2008/0183071 A1 | 7/2008 | Strommer et al. | |
| 2009/0093691 A1 * | 4/2009 | Krijnsen et al. | 600/302 |
| 2009/0221908 A1 | 9/2009 | Glossop | |
| 2009/0299176 A1 * | 12/2009 | Gleich et al. | 600/431 |
| 2010/0041990 A1 * | 2/2010 | Schlitt et al. | 600/439 |
| 2010/0298736 A1 * | 11/2010 | Levy | 600/566 |

FOREIGN PATENT DOCUMENTS

| | | |
|---|---|---|
| WO | 9631753 A2 | 10/1996 |
| WO | 9703609 A1 | 2/1997 |
| WO | 9927837 A2 | 6/1999 |
| WO | 9933406 A1 | 7/1999 |
| WO | 9958055 A1 | 11/1999 |
| WO | 9959055 A1 | 11/1999 |
| WO | 2004019799 A1 | 3/2004 |
| WO | 2004023103 A1 | 3/2004 |
| WO | 2007067323 A2 | 6/2007 |
| WO | 2009049082 A1 | 4/2009 |
| WO | 2009153723 A1 | 12/2009 |

* cited by examiner

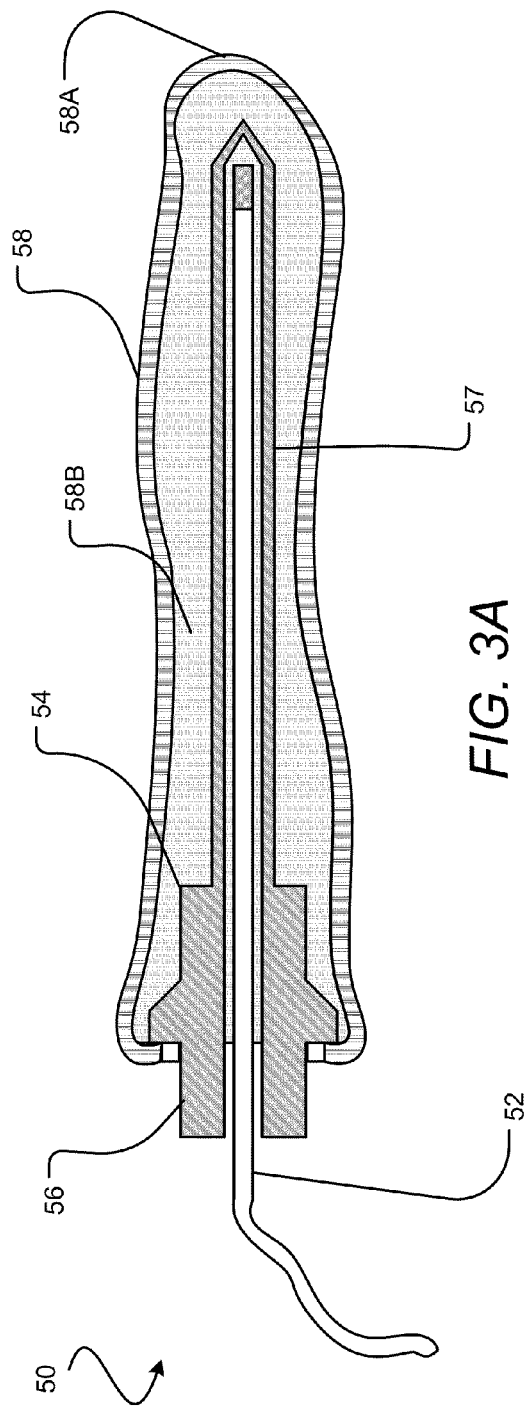
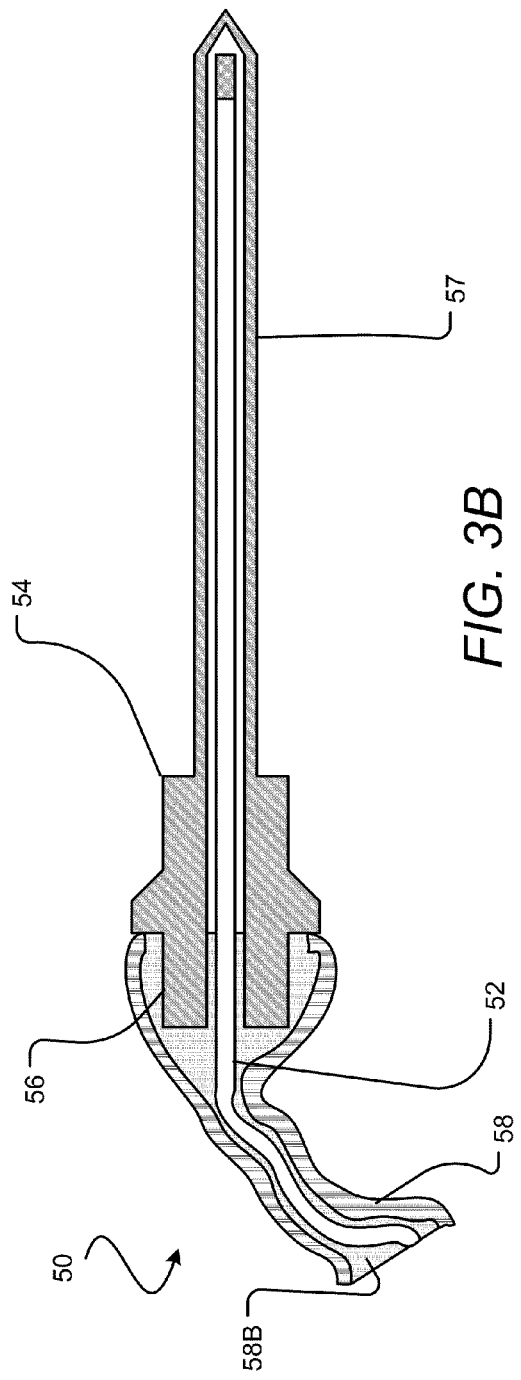
FIG. 3A
FIG. 3B

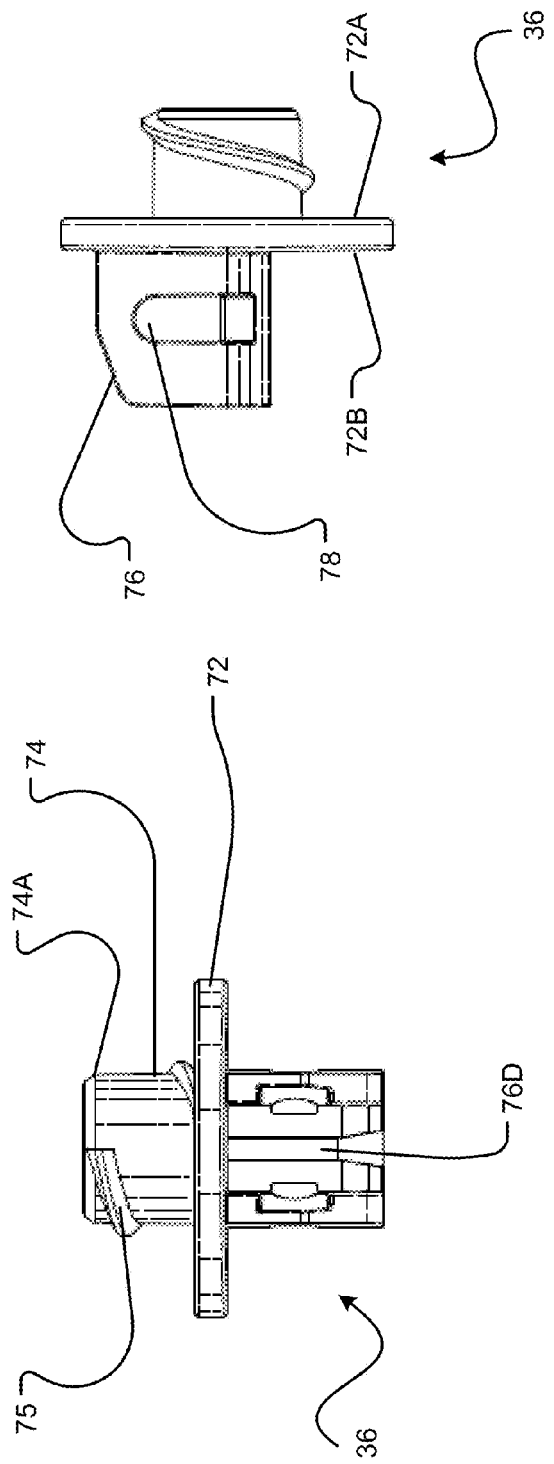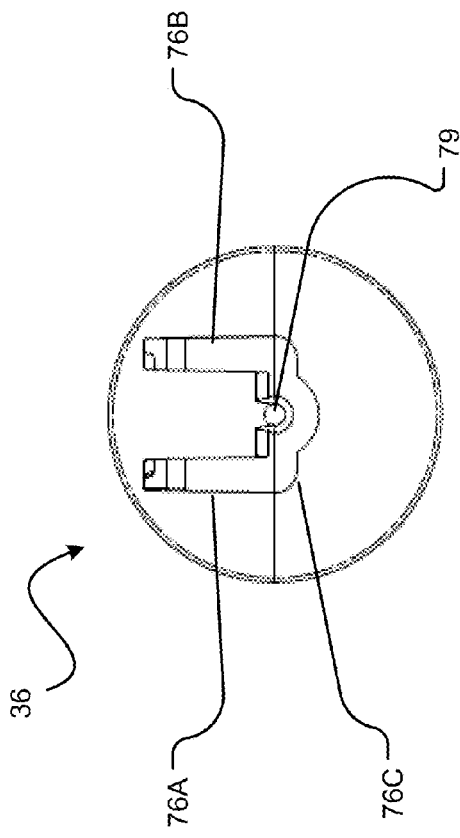
FIG. 5A
FIG. 5B
FIG. 5C

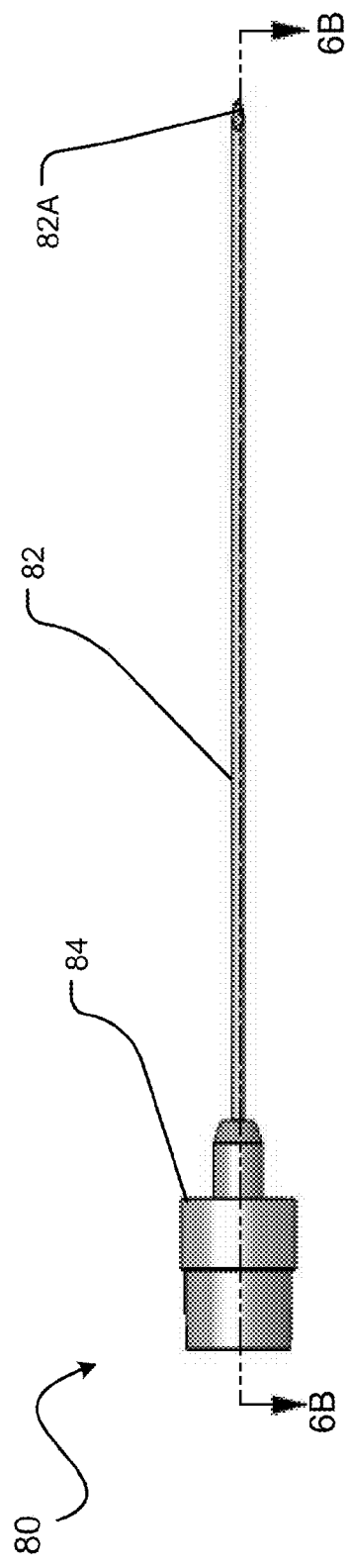
FIG. 6A
FIG. 6B

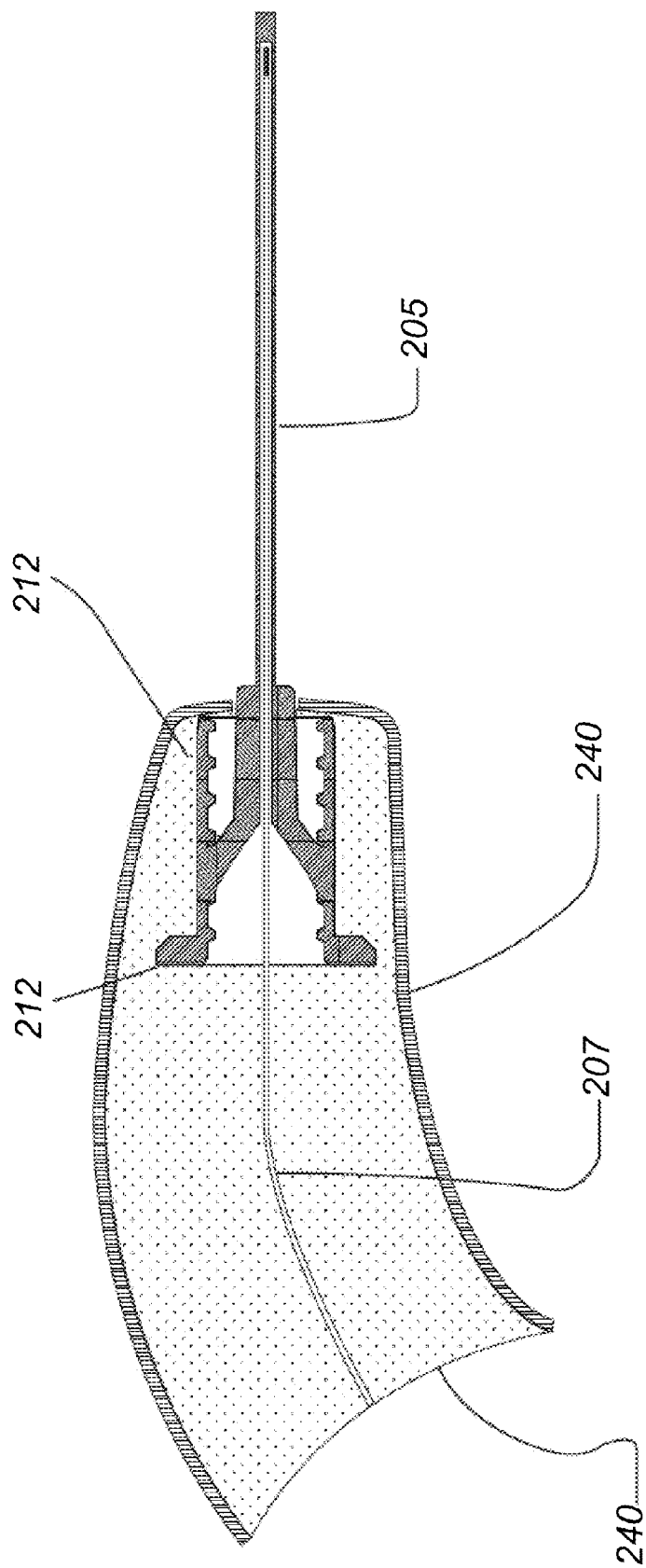

SPATIAL NEEDLE GUIDANCE SYSTEM AND ASSOCIATED METHODS

CROSS-REFERENCE TO RELATED APPLICATIONS

This invention claims the benefit under 35 U.S.C. §119 of U.S. Patent Application No. 61/293,546 filed on 8 Jan. 2010 and entitled SPATIAL NEEDLE GUIDANCE SYSTEM AND ASSOCIATED METHODS and U.S. Patent Application No. 61/393,788 filed on 15 Oct. 2010 and entitled SPATIAL NEEDLE GUIDANCE SYSTEM AND ASSOCIATED METHODS which are hereby incorporated herein by reference.

TECHNICAL FIELD

This invention relates to medical navigation technology. Embodiments of the invention have particular application in the fields of medical diagnosis and therapeutics involving the use of needles.

BACKGROUND

Needles are used in a wide range of medical applications. For example, needles are used in biopsy procedures. A biopsy typically involves identifying a tissue of interest, such as suspicious solid mass, a distortion in the structure of a body tissue, or an area of abnormal tissue change. A needle may be inserted into the abnormality and used to withdraw a small tissue sample for investigation.

Various types of needles may be used for biopsies. In fine needle aspiration, small hollow needles are used to extract cells from a location of interest. A core needle is a larger diameter needle which may be used to withdraw larger samples of tissue. Vacuum assisted devices may be used to collect multiple tissue samples during one needle insertion. In some cases medical imaging technologies are used to assist in placing a guide wire into a location of interest to assist a surgeon in locating the abnormality for a surgical biopsy.

A challenge in performing needle biopsies, or like procedures, is that the needle, or other thin member, and particularly the end thereof, must be placed at a desired location in the subject's body. Imaging of the subject's body and needle placed therein, such as ultrasound imaging or the like, may be used during needle insertion, and the resulting images used to help guide the needle to a desired location. A problem with using imaging in any of these procedures, or like procedures, is that the needles are often very difficult to see in an image. This makes it difficult for a person taking the biopsy to ensure that the needle has reached its target. Also, guiding the needle to place the tip of the needle at an area of a location shown in an image can take a significant amount of skill because the image does not always provide good feedback to the practitioner regarding exactly where the needle is placed and/or how the needle should be manipulated to cleanly enter tissue at the location. Also, the needle may not be visible in the image because all or part of the needle is out of the plane of the image.

Accurate needle placement is also important in a variety of medical procedures that involve delivering substances into the body of a subject using needles. For example, accurate placement may be required for the introduction of a drug, such as an anesthetic, or a radioactive seed for cancer treatment or the like.

The following US patents, US patent applications and other publications disclose technology that may be in the general field of this invention:

U.S. Pat. No. 7,599,730 to Hunter et al.;
U.S. Pat. No. 7,529,393 to Peszynski et al.;
U.S. Pat. No. 7,366,562 to Dukesherer et al.;
U.S. Pat. No. 7,221,972 to Jackson et al.;
U.S. Pat. No. 7,174,202 to Bladen et al.;
U.S. Pat. No. 6,920,347 to Simon et al.;
U.S. Pat. No. 6,785,571 to Glossop;
U.S. Pat. No. 6,764,449 to Lee et al.;
U.S. Pat. No. 6,733,458 to Stein et al.;
U.S. Pat. No. 6,317,616 to Glossop;
U.S. Pat. No. 6,216,029 to Paltieli;
U.S. Pat. No. 6,246,898 to Vesely et al.;
U.S. Pat. No. 5,868,675 to Henrion et al.;
U.S. Pat. No. 5,638,819 to Manwaring;
U.S. Pat. No. 5,443,489 to Ben-haim;
U.S. Pat. No. 5,211,165 to Dumoulin et al.;
U.S. Pat. No. 5,161,536 to Vilkomerson et al.;
U.S. Pat. No. 4,905,698 to Strohl Jr. et al.;
U.S. Pat. No. 4,173,228 to Van Steenwyck et al.;
U.S. Pat. No. RE41066 to Martinelli et al.;
U.S. Pat. No. RE40852 to Martinelli et al.;
US2009/0221908A1 to Glossop;
US2008/0183071 to Strommer et al.
US2007/0232882 to Glossop et al.;
US2007/0167787 to Glossop et al.;
US2006/0241577 to Balbierz et al.;
US2006/0184016 to Glossop;
US2005/0182295 to Soper et al.;
US2005/0085793 to Glossop;
US2004/097806 to Hunter et al.;
US2004/0267121 to Sarvazyan et al.;
WO 2007/067323 to Webler et al.;
WO 99/59055 to Vesely et al.;
WO 99/33406 to Hunter et al.;
WO 99/27837 to Paltieli et al.;
WO 97/03609 to Paltieli;
WO 94/24933 to Bucholz;
*Freehand 3D Ultrasound Calibration: A Review*, P-W. Hsu, R. W. Prager A. H. Gee and G. M. Treece CUED/F-INFENG/TR 584, University of Cambridge Department of Engineering, December 2007

BRIEF DESCRIPTION OF DRAWINGS

The accompanying drawings illustrate non-limiting embodiments.

FIG. 3A is a cross-sectional view of a sheathed position marker assembly according to an example embodiment.

FIG. 3B is a cross-sectional view of a sheathed position marker assembly according to an example embodiment.

FIG. 5A is side elevation view of a connector base according to an example embodiment.

FIG. 5B is top plan view of the connector base depicted in FIG. 3A.

FIG. 5C is an end elevation view of the connector base depicted in FIG. 3A.

FIG. 6A is a side elevation view of a sheath according to an example embodiment.

FIG. 6B is a cross-section of the sheath depicted in FIG. 4A.

FIG. 12 is a cross section through an example position sensor assembly showing how the position sensor assembly may be applied in combination with a sterile sleeve enclosure.

DESCRIPTION

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive, sense.

One aspect of the invention relates to methods and apparatus to facilitate monitoring the location of the tip or other point on a thin elongate member such as a needle. Embodiments of such methods and apparatus may be applied, for example, to monitor the position of the tip of a biopsy needle, the tip of a needle to be used to delivery anaesthetic or another fluid, the tip of a probe, the tip of a brachytherapy applicator, an electrode, a hollow guide for introducing other instruments, or the like. In some embodiments, an image of tissues into which the needle is to be placed is registered to the coordinate system in which the position of the needle tip is to be monitored. In such embodiments the actual position of the needle tip, the desired location of the needle tip and anatomical structures within the tissue may be displayed.

Figure 1:
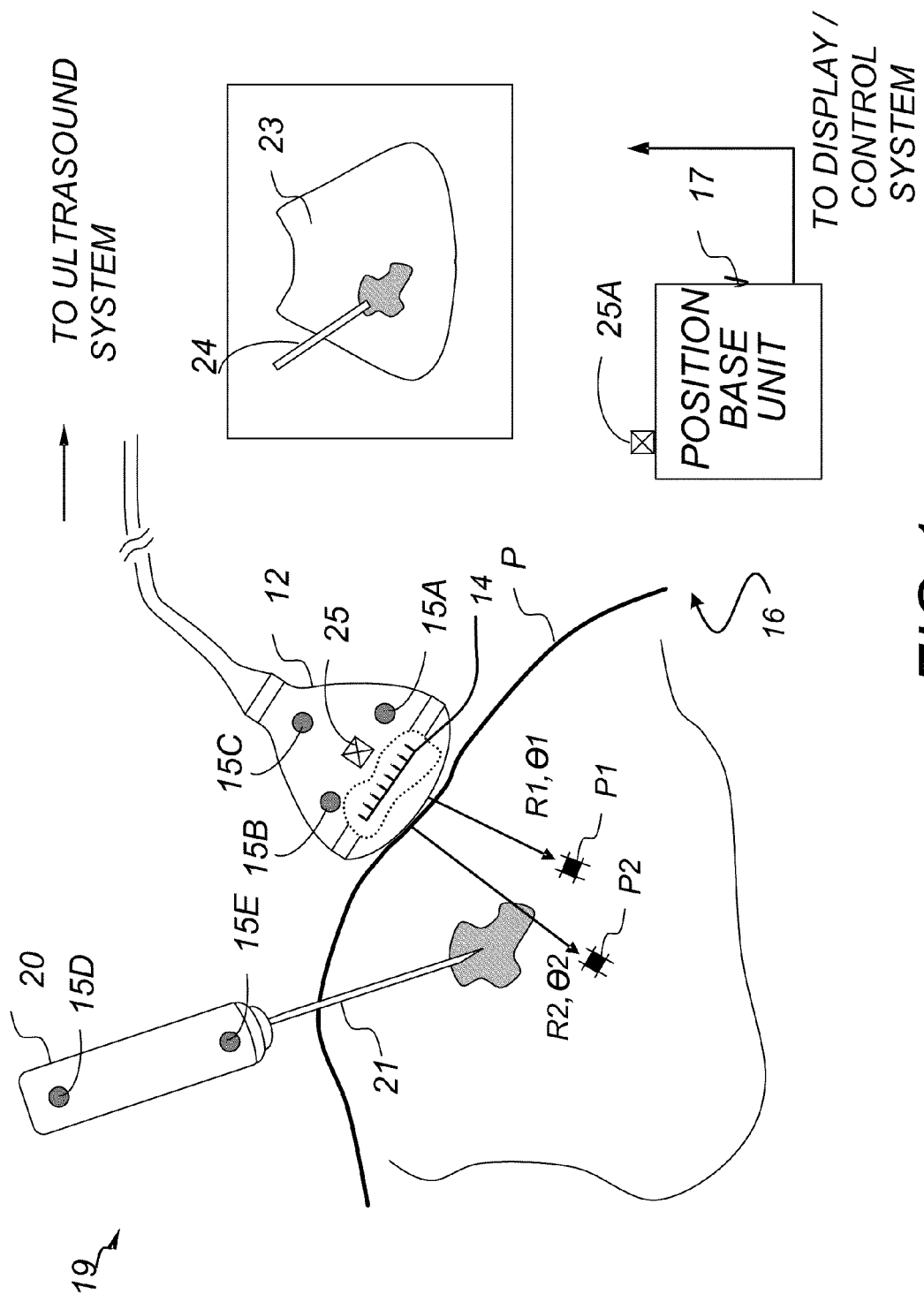
FIG. 1 is a schematic view of an example ultrasound probe and biopsy assembly as may be used with the invention.

FIG. 1 shows an example application in which a position sensing system is provided. The position sensing system monitors positions of location markers that are associated with various implements. Various position sensing systems are commercially available. In FIG. 1 a positioning sensing system 16 monitors positions and orientations of an ultrasound probe 12 and a biopsy apparatus 19.

The position and orientation of probe 12 are monitored by a 3D position sensor system 16. The 3D position sensor system 16 may include one or more position sensor base units and one or more markers carried on probe 12. In the illustrated embodiment, probe 12 includes a plurality of position markers 15. In the illustrated embodiment, there are three position markers, 15A, 15B, and 15C. Position markers 15A, 15B, and 15C are not located along a common line. Therefore, if the locations of position markers 15A, 15B, and 15C are known, the position and orientation in space of probe 12 is uniquely determined. Since the particular cross section represented by an ultrasound image depends upon the current position and orientation of a transducer array 14 in probe 12, the position and orientation of ultrasound images can be determined from the position and orientation in space of probe 12.

The positions of location markers 15 relative to a global coordinate system are measured by 3D position sensor system 16. In the illustrated embodiment the sensor system includes a position base unit 17. 3D position base unit 17 and position markers 15 may comprise any suitable technology. For example, 3D position base unit 17 may detect electromagnetic or other fields emitted by position markers 15 or vice versa. In some embodiments position base unit 17 generates a magnetic field that is sensed by position markers 15. A 3D position sensing system may, for example, comprise a medSAFE™ or drive BAY™ position sensor available from Ascension Technology corporation of Burlington, Vt., USA.

Some 3D position sensing technologies permit both the location and orientation of a single position marker to be determined. Where such 3D position sensing technologies are used, fewer position markers 15 are required to determine the location and orientation of an implement such as probe 12 than would be the case for position markers for which only position is determined. For example a single 6 degree of freedom position marker may be used in a compatible position sensor system to obtain both position and orientation information for a probe 12. A 3 degree of freedom position marker may be used in a compatible position sensor system to obtain position information in three coordinate directions. In some embodiments one or more redundant position markers 15 may be provided. In embodiments which provide more position markers than are required to identify position and orientation of probe 12, positions of the additional position markers may be monitored by 3D position base unit 17 and used to provide information regarding the position and orientation of probe 12 of enhanced accuracy.

The ultrasound system may generate images of tissues in the field of view of probe 12. For example, in so-called B-mode imaging, a 2D image of a selected cross-section of the patient's body is generated. Because the position and orientation of transducer array 14 is fixed in probe 12, the particular cross section represented by an ultrasound image depends upon the current position and orientation of probe 12 relative to the patient's body. Moving probe 12 relative to the patient's body will result in a different cross section being imaged.

FIG. 1 shows two scattering locations, P1 and P2. P1 is located at position R1, θ1. P2 is at location R2, θ2. These locations are both determined with reference to a coordinate system that can be considered to be attached to probe 12.

FIG. 1 also shows a biopsy apparatus 19 which includes a handle 20 and a needle 21. Biopsy apparatus 19 includes one or more position markers 15. In the illustrated embodiment, there are two position markers 15, individually identified as 15D and 15E. In the illustrated embodiment, position markers 15D and 15E are located so that they correspond to reference positions on an extension of a longitudinal axis of needle 21. Neglecting rotations about the axis of needle 21, the position and orientation of needle 21 can be uniquely determined if the positions of position markers 15D and 15E are known. In the illustrated embodiment, the reference positions of location markers 15D and 15E are monitored by 3D position sensor system 16.

It can be appreciated that the apparatus illustrated in FIG. 1 may facilitate the placing of needle 21 into the body of patient P such that needle 21 may be used to acquire a tissue sample or place something at a desired location within patient P. Specifically, when an ultrasound image 23 is generated from ultrasound data acquired by probe 12, the precise location and orientation of needle 21 relative to that ultrasound image can be determined from the known locations of position markers 15 on probe 12 and biopsy assembly 19. Having this information allows the location of needle 21 to be illustrated clearly on image 23 (even if the ultrasound echos do not provide a clear image of needle 21). In the illustrated embodiment, needle 21 is represented by a computer-generated line 24 that shows the position of needle 21 in image 23, as calculated connector based on the relative positions of position markers 15.

The precise location and orientation of needle 21, and of features thereon, relative to that ultrasound image can be determined from the known locations of position markers 15 on probe 12 and biopsy assembly 19 using procedures, such as those described in co-pending application 61/252,377 filed on 16 Oct. 2009 and entitled Ultrasound Systems Incorporating Spatial Position Sensors and Associated Methods, and in *Freehand 3D Ultrasound Calibration: A Review*, P-W. Hsu, R. W. Prager A. H. Gee and G. M. Treece CUED/F-INFENG/TR 584, University of Cambridge Department of Engineering, December 2007, both of which are hereby incorporated herein by reference.

Having knowledge of the location of needle 21 relative to the plane at which an ultrasound image 23 is obtained can permit the calculation and display of images and other feedback that helps a user to visualize the relative locations of needle 21 and a targeted abnormality or other location within a patient P. Examples of such displays and other feedback are disclosed in co-pending application 61/252,377.

In the embodiment illustrated in FIG. 1, position markers 15D and 15E are built into a handle of biopsy apparatus 19. Needle 21 is detachably affixable to the handle. The position and orientation of needle 21 determined from the positions of position markers 15D and 15E is accurate only if position markers 15D and 15E are located at their reference positions with respect to needle 21. The accuracy of the position of the tip of needle 21 and the orientation of needle 21 may suffer if needle 21 bends or is otherwise moved or deformed. It may be difficult or impossible to know if position markers 15D and 15E are located at their reference positions with respect to needle 21 when needle 21 is in use.

One aspect of the invention relates to methods and apparatus for supporting a position marker at a pre-determined location within a casing that is configured for use with a thin elongate member. Embodiments of such methods and apparatus may be applied, for example, to provide a position sensor system that may be used to monitor the position of the tip of a needle in a sterile environment.

Figure 2:
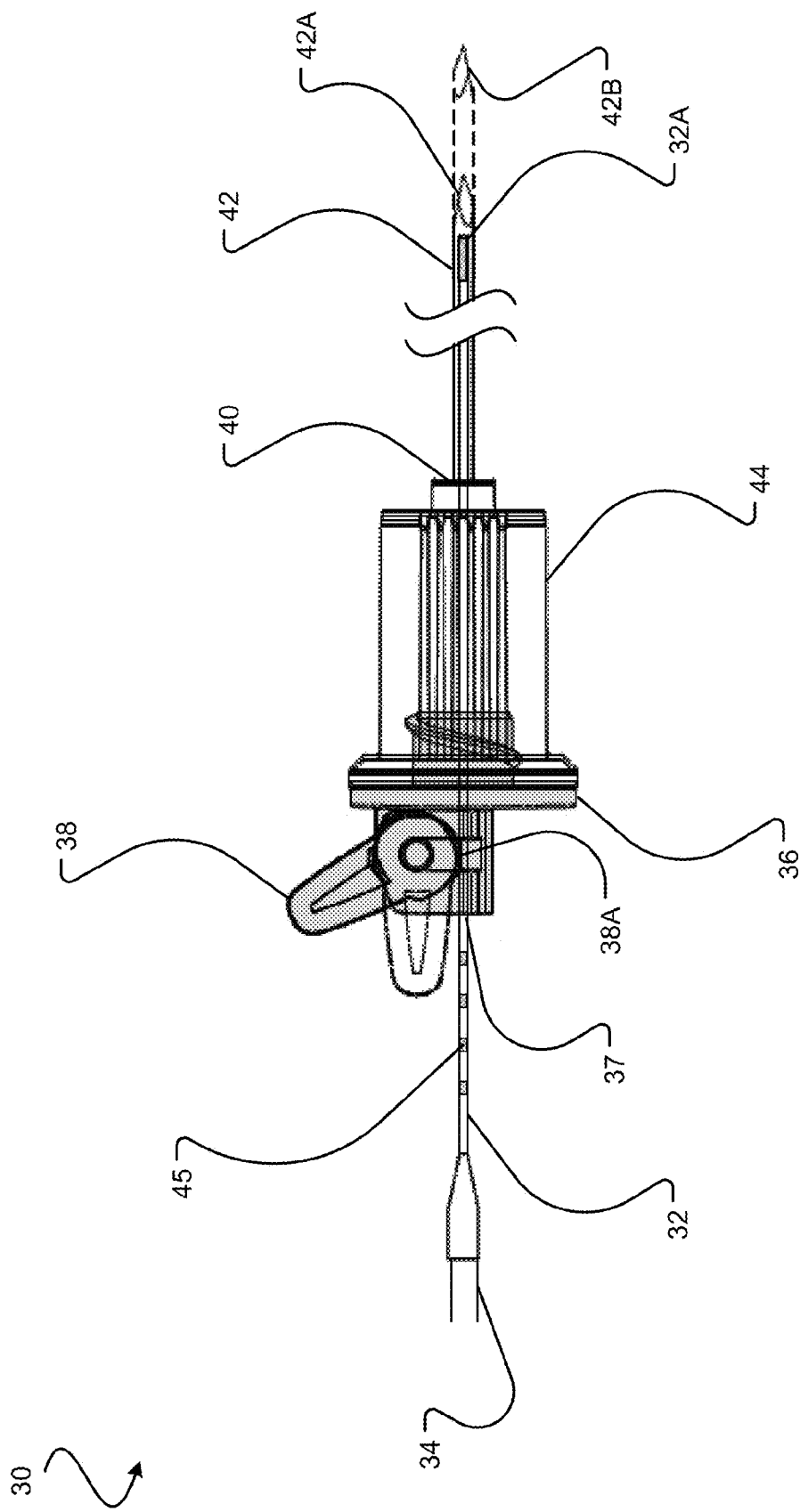
FIG. 2 is a side elevation view of a sheathed position marker assembly according to an example embodiment.

FIG. 2 is a side elevation view of a sheathed position marker assembly 30 according to an example embodiment. A position marker 32A is located at the end of sensor cable 32. The position of marker 32A can be detected by position sensor 34. Position marker 32A may comprise a six-degree of freedom position marker that may be used with a compatible position sensor to obtain both position and orientation or a three-degree of freedom position marker that provides position information, for example. Sensor cable 32 extends through an aperture 37 in connector base 36 into sheath 40. Sheath 40 comprises a hollow shaft 42 extending from a hub 44. Tip 42A of shaft 42 is closed. Position marker 32A is positioned inside hollow shaft 42 of sheath 40.

The location of position marker 32A inside sheath 40 is fixed by the coupling of sensor cable 32 to connector base 36 by a releasable attachment device shown as clip 38. In the illustrated embodiment, clip 38 comprises a cam 38A configured for releasable locking frictional engagement with sensor cable 32 by the pivoting of clip 38. In use, clip 38 may be pivoted so that cam 38A clears aperture 37. When cam 38A clears aperture 37, position marker 32A may be slid into shaft 42 of sheath 40. Position marker 32A and/or sensor cable 32 may be placed in a predetermined spatial relationship with sheath 40. In some embodiments, the predetermined relationship is defined, at least in part, by the abutment of sensor 32A against tip 40A of shaft 42. When sensor cable 32 extends through aperture 37 of connector base 36, clip 38 may be pivoted so that cam 38A develops locking friction against sensor cable 32 to clamp sensor cable 32 against connector base 36 and thereby securely fix the relative positions of position marker 32A and sheath 40.

In the embodiment illustrated in FIG. 2, connector base 36 is detachably coupled to hub 44 of sheath 40. This is optional. In the illustrated embodiment the detachable coupling is provided by a threaded connection. Connector base 36 and hub 44 may be detachably engageable by other types fittings. Connector base 36 and hub 44 may comprise fittings commonly used in the medical and/or laboratory instruments. For example, in some embodiments, connector base 36 comprises a male Luer type connector and hub 44 comprises a corresponding female Luer type connector. A variety of other connectors may be used to connect connector base 36 and hub 44, such as, for example, Luer-Lok™, Luer-Slip™ connectors, or the like. In some embodiments, hub 44 is a standardized needle hub, such as, for example, a Hart™ SG IV Hub.

In alternative embodiments, connector base 36 may be omitted and means for fixing the relative positions of position marker 32A and sheath 40 may be provided on sheath 40. For example, a clip similar to clip 38 or other suitable clamping mechanism may be mounted on hub 44.

In the embodiment illustrated in FIG. 2, sensor cable 32 comprises optional markings 45 indicative of the distance along sensor cable 32 from position marker is 32A. Such markings may be used in locating position marker 32A in sheath 40. For example, the alignment of markings on sensor cable 32 with a feature on connector base 36 may correspond to pre-determined spatial relationships between position marker 32A and sheath 40. In some applications, sensor cable 32 and position marker 32A may be used with sheaths having shafts of different lengths, such as the sheath having tip 42B. Embodiments configured for such applications may provide markings on sensor cable 32 that locate position marker 32A near the ends of corresponding sheaths when the markings are aligned with connector base 36.

Using markings to locate position marker 32A in sheath 40 can help avoid damage to position marker 32A that may be caused by contact between position marker 32A and the end of sheath 40. In some embodiments, markings are configured to locate position marker 32A at a distance more than 0.25 centimeters from the end of sheath 40. In some embodiments, markings are configured to locate position marker 32A at a distance less than 2 centimeters from the end of sheath 40. Markings may be coded by color, pattern or the like to indicate particular spatial relationships with position marker 32A.

It will be appreciated that sensor cable 32 may have a wide range of constructions. Any suitably fine elongate member may be used for sensor cable 32. For example, position marker 32A may be provided on the end of a needle. The needle may be inserted into sheath 40, causing position marker 32A to move further along the sheath 40. When position marker 32A is aligned with the tip 42A of sheath 40, the needle may be locked in place at connector base 36 by cam 38A, thereby fixing the location of position marker 32A at tip 42A. In some embodiments, sensor cable 32 comprises conductors for carrying signals from position marker 32A to a position sensor (not shown in FIG. 2). In some embodiments, a plurality of position markers may be attached to sensor cable 32. In some such embodiments, position markers may be attached at spaced apart locations along sensor cable 32.

Hollow shaft 42 of sheath 40 may comprise rigid or flexible materials. In some embodiments hollow shaft 42 is formed of resilient semi-rigid plastic. In other embodiments, hollow shaft 42 is formed of metal such as a suitable stainless steel. In some embodiments, at least part of hollow shaft is transparent or translucent. In some embodiments, hollow shaft has a gauge of less than 20. Hollow shaft 42 may comprise characteristics of commonly available medical needles. For example, tip 42A may comprise a trifacet trocar tip, a Franseen-type tip, a pencil tip stylet, or the like. In some embodiments, sheath 40 comprises a closed-ended hollow needle.

FIGS. 3A and 3B show cross-sectional views of a sheathed position marker assembly 50. Sheathed position marker assembly 50 comprises a sheath 54 that encases a sensor cable 52 and a position marker 52A located at the end of sensor cable 52. Sheath 54 comprises a hub 56 joined to a hollow shaft 57 and a tubiform cover 58 attached to hub 56. In FIG. 3A cover 58 is shown in a first configuration in which it extends from hub 56 to enclose shaft 57 of sheath 54. While cover 58 is in the first configuration, sensor cable 52 and position marker 52A may be inserted into sheath 54 and coupled to sheath 54. In some embodiments, shaft 57 and cover 58 may be translucent or transparent to facilitate positioning of position marker 52A in shaft 57 while cover 58 is in the first configuration.

In the embodiment illustrated in FIG. 3A sheath 54 is provided in a sterile first configuration in which end 58A of cover 58 is closed to maintain a sterile condition within cover 58. The sterile condition may comprise, for example, a condition in which hub 56, shaft 57, and the surface 58B of cover 58 that faces shaft 57 are sterile. In embodiments where sheath 54 is provided in a sterile first configuration, a non-sterile position marker 52A and sensor cable 52 may be inserted into sheath 54 while sheath 54 is in the first configuration.

In FIG. 3B cover 58 is shown in a second configuration in which it extends from hub 56 over the portion of sensor cable 52 that is outside of sheath 54. Cover 58 is changed from the first configuration to the second configuration by drawing end 58A of cover 58 toward and past hub 56. In the process of changing cover 58 from the first configuration to the second configuration, cover 58 is turned inside-out, such that the surface 58B of cover 58 that faces shaft 57 in the first configuration faces the surrounding environment in the second configuration.

Where end 58A of cover 58 is closed in the first configuration, changing cover 58 from the first configuration to the second configuration may involve puncturing or opening cover 58. In some embodiments, cover 58 comprises a slit, a peel tab, or the like to facilitate opening end 58A for changing cover 58 from the first configuration to the second configuration. Such embodiments may permit position marker 52A to be located and fixed in sheath 54 while sheath 54 is in a non-sterile environment (for example, away from a patient), and the sheathed position marker assembly subsequently provided in a sterile condition as required. In alternative embodiments, sheath 54 is provided in a sterile first configuration in which end 58A of cover 58 is open. Such embodiments may comprise a clip or the like for closing the open end 58A of cover 58.

Cover 58 may comprise any suitably flexible material. In some embodiments, cover 58 comprises elastic material. In some embodiments, cover 58 comprises a thin flexible plastic. A cover comprising elastic material may stretch when drawn past hub 56, thereby facilitating the transition of the cover from the first configuration to the second configuration. A cover comprising elastic material may also conform to the portion of sensor cable 52 that extends outside of sheath, thereby providing a tidier assembly.

Cover 58 may be permanently or removably affixed to sheath 54. For instance, in some embodiments, cover 58 comprises a circumferential elastic band that conforms to the surface of hub 56. In some such embodiments, hub 56 comprises a groove configured for seating the elastic band. In some embodiments, a clip (not shown) is provided for retaining a section of cover 58 against hub 56. In some embodiments, cover 58 may be permanently secured to sheath 54 by adhesive, thermal bonding, or the like.

Sheathed position marker assemblies 30 and 50 may be inserted into a hollow elongate member to form a position tracked member assembly. Where the sheath of the sheathed position marker assembly is in a known spatial relationship with the elongate member to be positioned then position information concerning the member may be obtained from the position of the marker as determined by the position sensor. Where information from the position sensor is used to generate a visual display of the location of the position marker, an image of a body showing an indication of the position of the position marker within the body, such as by a computer generated cursor, will incidentally indicate the position the member. Thus guidance information derived for the position marker may be used to position the elongate member at a desired location in the body of a subject. Guidance information may be generated and/or presented in a wide variety of forms, including any described in co-pending application 61/252,377.

Figure 4:
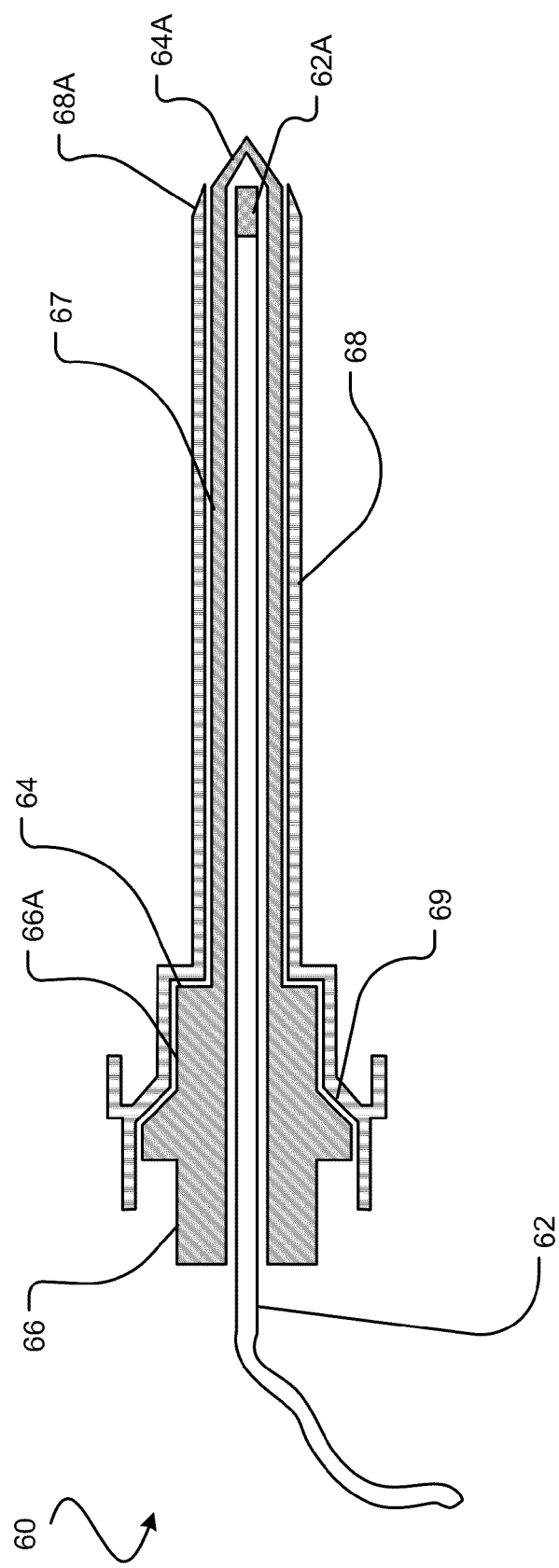
FIG. 4 is a cross-sectional view of a position tracked member assembly according to an example embodiment.

FIG. 4 shows a cross-sectional view of an example position tracked instrument assembly 60. Assembly 60 comprises a sheath 64 that encases an end of a sensor cable 62 and a position marker 62A located at the end of sensor cable 62. Sheath 64 is located in a hollow needle 68. The tip 64A of sheath 64 is pointed and extends past the tip 68A of hollow needle 68. Tip 68A of hollow needle 68 is beveled.

In assembly 60, sheath 64 is coupled to hollow needle 68 by the connection of fitting 66A of hub 66 to fitting 69 of hollow needle 68. Sheath 64 and needle 68 are configured such that position marker 62A in sheath 64 is substantially aligned with tip 68A of needle 68 when fitting 66A is connected with fitting 69. Fitting 66A and fitting 69 may comprise, for example, fittings commonly used in medical and/or laboratory instruments. For example, in some embodiments, fitting 66A comprises a male Luer lock connector and fitting 69 comprises a female Luer lock connector. A variety of other connectors may be used to connect fitting 66A and fitting 69, such as, for example, Luer-Lok™, Luer-Slip™ connectors, Hart™ SG IV hub connectors. Providing fitting 69 with a type of fitting commonly used in medical and/or laboratory instruments may permit needle 68 to be connected to other medical and/or laboratory instruments when sheath 64 is removed. Needle 68 may comprise a commercially available type of needle adapted for a particular purpose, such as, for example, a biopsy needle, a vascular needle, a nerve access needle, or the like. Proprietary couplings may also be used.

Assembly 60 may be used to position hollow needle 68 at a desired location in a body as described above. After hollow needle 68 has been positioned at the desired location, sheath 64, sensor cable 62 and position marker 62A may be removed from the body. Hollow needle 68 may then be used for a medical purpose, such as, for example, obtaining a biopsy sample at the location, guiding another instrument to the location, or delivering medication to the location. It will be appreciated that it is not necessary that hollow needle 68 be a needle, and that any suitably fine elongate hollow member into which sheath 64 may be inserted may be provided in place of hollow needle 68. It will further be appreciated that it is not necessary that tip 68A of hollow needle 68 be open for some applications.

In some embodiments, sheath 64 of assembly 60 may be provided with a tubiform cover (not shown in FIG. 4), such as a cover like cover 58 shown in FIGS. 3A and 3B. In some such embodiments, sheath 64 may be coupled to hollow needle 68 while the cover extends from hub 66 toward tip 64A of sheath 64. In other embodiments, the cover may be provided after sheath 64 and hollow needle have been coupled. In this manner, a sheath having a sterile exterior can be coupled with a sterile hollow needle, and the sterile condition of the assembly formed thereby may be protected from contamination by the cover.

FIGS. 5A, 5B and 5C are respectively, a top plan view, a side elevation view and an end elevation view of an example connector base 36. Connector base 36 comprises a transverse wall 72. Hollow cylinder 74 projects from a first side 72A of wall 72. The outside surface of the end of cylinder 74 remote from wall 72 comprises a taper 74A. Helical threads 75 are provided on the exterior surface of cylinder 74 for mating with corresponding threads of a hub (not shown). U-shaped bracket 76 projects from a second side 72B of wall 72 opposite first side 72A. Bracket 76 comprises opposed bracket walls 76A and 76B and bottom portion 76C. Transverse apertures 78 are defined through bracket walls 76A and 76B for receiving tabs of a clip (not shown). A longitudinal aperture 79 extends through connector base 36 and defines a channel 76D in bottom portion 76C of bracket 76. Aperture 79 and channel 76D are configured for receiving a position marker and a sensor cable (not shown).

FIG. 6A is a side elevation view of sheath 80 according to an example embodiment. A hollow shaft 82 extends from a hub 84 of sheath 80. Tip 82A of shaft 82 comprises a trifacet trocar tip. FIG. 6B shows a cross-sectional view of sheath 80 along line 6B. The side of hub 84 adjacent shaft 82 comprises a male Luer lock fitting 86. The side of hub 84 opposite shaft 82 comprises a female Luer lock fitting 88. In some embodiments, female Luer lock fitting 88 is connectable to a male Luer lock fitting of a connector base (not shown). In some embodiments, male Luer lock fitting 86 is connectable to a female Luer lock fitting of a hollow elongate member (not shown). Shaft 82 may be configured to have a length such that when connected to a particular hollow elongate member, tip 82A is aligned with the end of the member. It will be appreciated that it is not necessary that the fittings on hub 84 be Luer lock fittings, or be the same style of fitting. It will be further appreciated that sheaths may be connected to connector bases and/or hollow elongate members with any suitable paired fittings.

Figure 7:
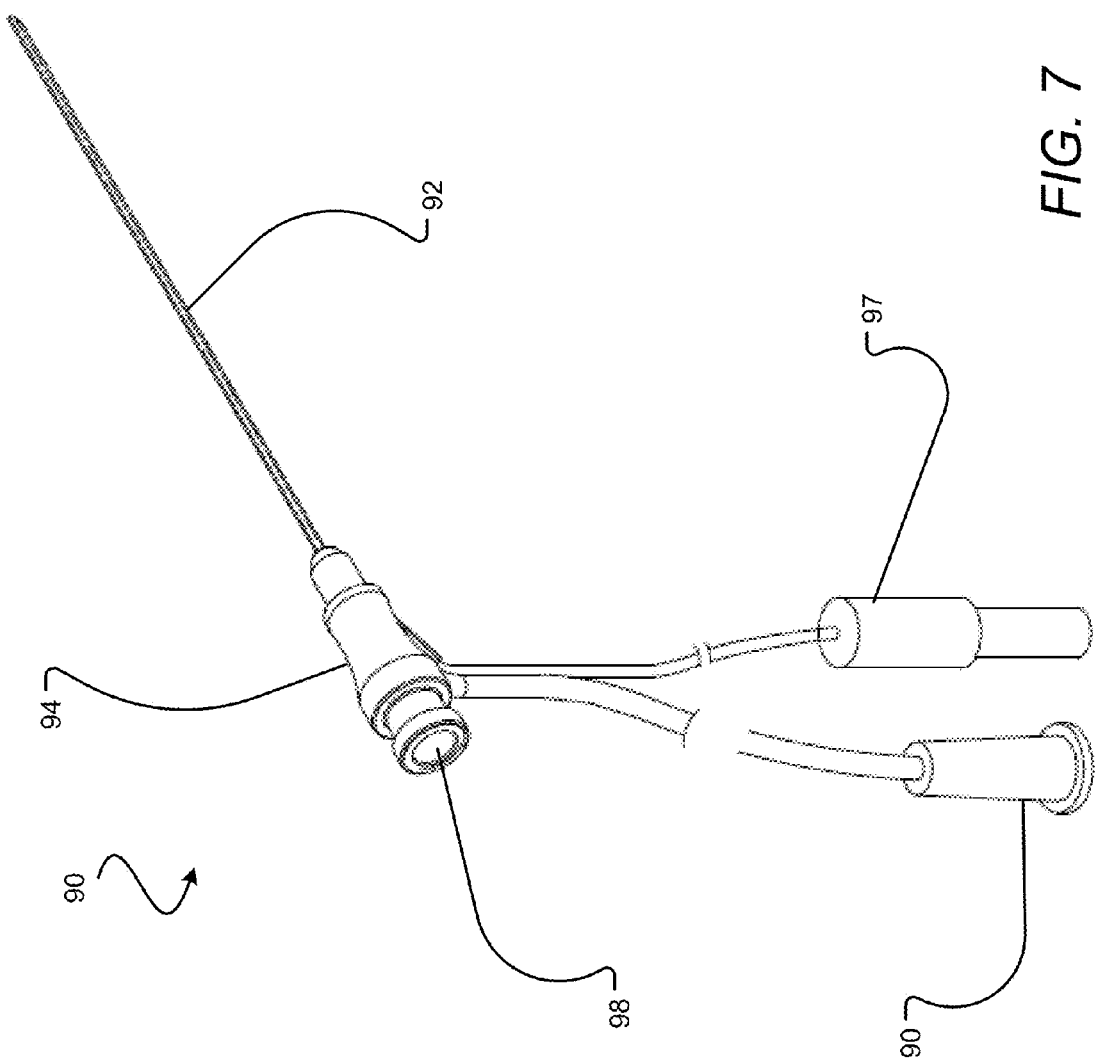
FIG. 7 is an isometric view of a nerve access needle according to an example embodiment.

FIG. 7 is an isometric view of a nerve access needle 90 according to an example embodiment. A hollow shaft 92 extends from a hub 94 of nerve access needle 90. A catheter tube 96 and/or electrostimulator cable 97 are connected to hub 94 for fluid communication with the lumen of shaft 92. Hub 94 comprises a sealing membrane 98. A sheath assembly as described herein (not shown in FIG. 7) may be inserted into the lumen of needle 90 by piercing membrane 98. After needle 90 has been positioned at a desired location in the body of a subject, the sensor needle may be removed, and membrane 98 sealed. When membrane 98 is sealed, fluid from tube 96 may be delivered to the lumen of shaft 92.

In some embodiments, membrane 98 is a self-sealing membrane. In other embodiments, membrane 98 is sealable by the application of heat, adhesive or other means. In some embodiments, hub 94 has an aperture in place of membrane 98, or a rim defining an aperture about membrane 98. A stopper may be provided for sealing the aperture after needle 90 has been positioned in the body of a patient and the sensor needle removed. In some such embodiments, the stopper may be tethered or otherwise attached to hub 94. The stopper may be shaped for sealing engagement with the aperture, and may comprise a fitting configured for engagement with a fitting about the aperture.

Figure 8:
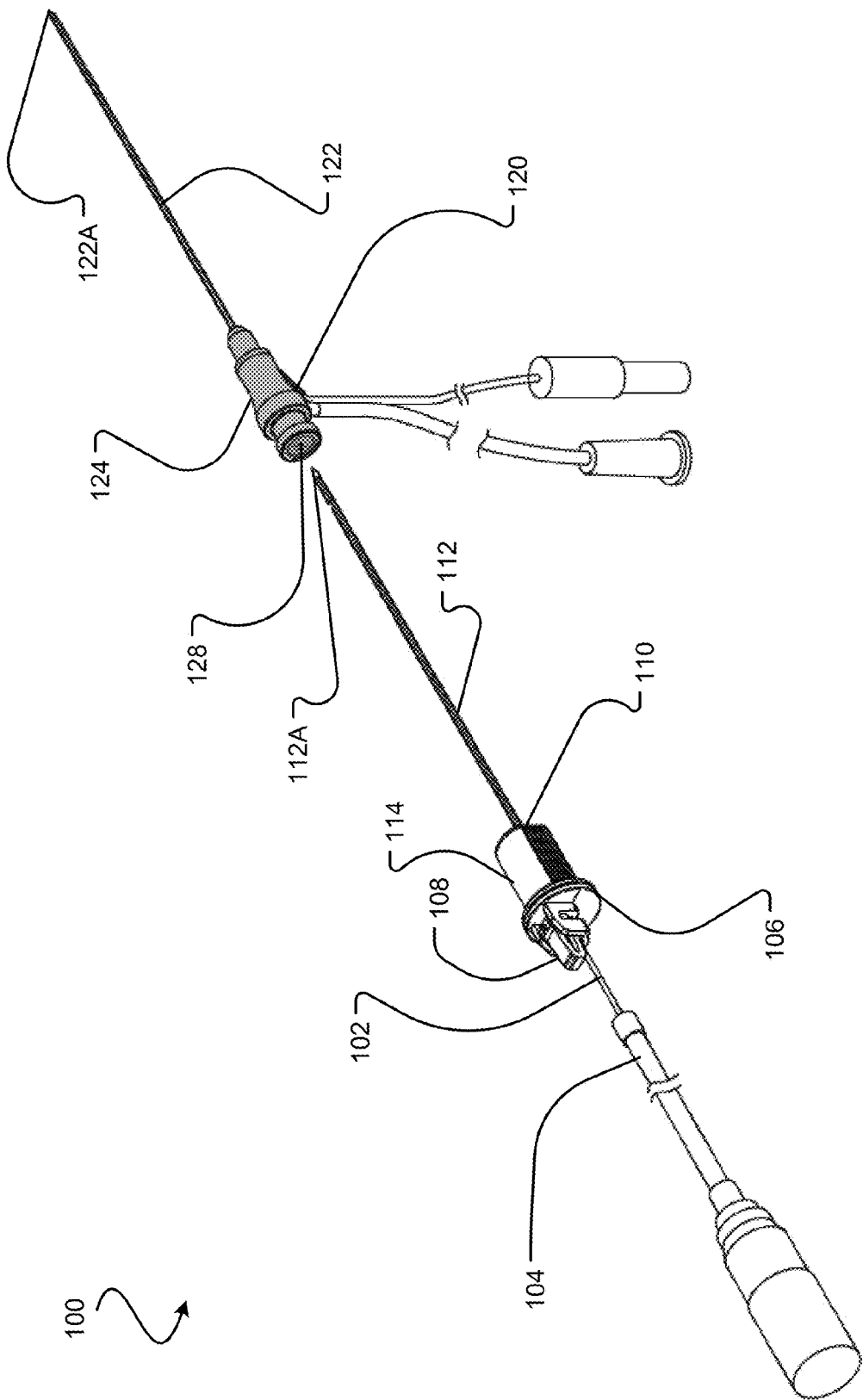
FIG. 8 is an isometric view of a needle sheath assembly according to an example embodiment.

FIG. 8 is an isometric view of a position tracked instrument assembly 100 according to an example embodiment. A sensor cable 102 carrying a position marker (not shown) is inserted through connector base 106 into a sheath 110. Sheath 110 comprises a closed-ended hollow shaft 112 extending from a hub 114. Connector base 116 is securely engaged with hub 102. Clip 108 is pivotally mounted on connector base 106 for releasable locking frictional engagement with sensor cable 102. A nerve access needle 120 comprises a hollow shaft 122 extending from a hub 124. Shaft 122 and hub 124 together are slightly shorter than shaft 112 so that a position marker at the end of shaft 112 will be located near or at the tip of shaft 122. Hub 124 comprises a sealing membrane 128.

Sheath 110 can be inserted into needle 120, and hub 114 positioned in abutment with hub 124. In some embodiments, the facing sides of hubs 114 and 124 are configured for fitting engagement. Since shaft 122 and hub 124 together have slightly shorter than shaft 112, placing hub 114 in abutment with hub 124 will cause shaft 112 to be coincident with shaft 122 for most of its length. It will be appreciated that shaft 112 need not extend all, or even most, of the length of shaft 112.

Sensor cable 102 may be inserted into sheath 110 and aligned for coincidence with sheath 110 before or after sheath 110 is inserted into needle 120. Connector base 106 and clip 108 may be used to securely fix the position of sensor cable 102 relative to sheath 110. With a position marker (not shown) attached to the end of sensor cable 102 coincident with tip 112A of sheath 110 and with tip 122A of needle 120, information from a position sensor 104 may be used to position needle 120 at a desired location inside a subject's body. After needle 120 has been positioned at the desired location, sensor cable 102 and sheath 110 and may be removed, either together or in order.

Connector base 106 may be used to seal a puncture in membrane 128. In some embodiments, connector base 106 comprises a fitting that is connectable to a fitting on hub 124. In some embodiments, clip 108 is configured for sealing a puncture in membrane 128 when connector base 106 is connected to hub 124. In some such embodiments, clip 108 is configured for both frictional engagement with sensor cable 102 (in a first position) and for sealing a puncture in membrane 128 (in a second position). It will be appreciated that in alternative embodiments, connector base 106 may comprise other means for frictionally engaging sensor cable 102 and/or sealing a puncture in membrane 128.

Connector base 106 may be used to seal an aperture of hub 124 that accommodates the insertion of sheath 110 into needle 120. In some embodiments, connector base 106 comprises a fitting that is sealingly engageable to a fitting on hub 124 for sealing such an aperture. In some such embodiments, the aperture may be sealed by connector base 106 independent of membrane 128. In some embodiments, clip 108 is configured to seal a longitudinal aperture (not shown in FIG. 8) that extends through connector base 106. In some such embodiments, clip 108 is configured for both frictional engagement with sensor cable 102 (in a first position) and for sealing the longitudinal aperture of connector base 106 (in a second position). It will be appreciated that in alternative embodiments, connector base 106 may comprise other means for frictionally engaging sensor cable 102 and/or sealing the longitudinal aperture of connector base 106.

Those skilled in the art will appreciate that sheath 110 may provide a barrier between sensor cable 102 and hollow needle 120. In some embodiments, sheath 110 is disposable. In some such embodiments, shaft 112 of sheath 110 comprises a plastic sleeve. In some embodiments connector base 106 is reusable. It will be appreciated that a non-sterile connector base 106, sensor cable 102, and position marker (not shown) may be combined with a sheath 110 having a sterile exterior to form a sheathed position marker assembly suitable for use in a sterile medical environment.

Application of the invention is not limited to taking biopsy samples. For example, apparatus and methods described herein may be applied to positioning needles and other fine members at desired locations within a body for the introduction of a drug, such as a anesthetic, or a radioactive seed for cancer treatment or the like. For example, the system may be used to position a catheter to introduce an epidermal anesthetic. The system may also be used, for example, for inserting catheters into organs, vessels and other anatomical structures.

An advantage of some embodiments is that the position marker is co-located with the same feature of the member being positioned that it is desired to place in a specific location. The feature may be a tip of the member for example. As another example, the feature may comprise an opening in a side of the member (such openings are found, for example, in some biopsy needles). Thus, certain calibration steps are avoided. Furthermore, the member may be flexible. Even if the member flexes during insertion, the actual position of the tip or other feature of the member can be monitored.

It can be appreciated that the apparatus and methods described herein have application in a wide range of imaging applications. For example, the methods and apparatus may be applied to:
  obtaining biopsy samples;
  placing radioactive seeds for cancer treatment or the like;
  placing electrodes;
  injecting drugs at specific locations;
  inserting an epidural catheter, for example for the introduction of an anaesthetic;
  injecting epidural anaesthetic;
  positioning surgical tools for minimally-invasive surgery;
  etc.

In embodiments which apply a position sensing technology based upon magnetic fields it is desirable to ensure that the sheath and any other parts of the apparatus do not distort magnetic fields in a way that would interfere with the accuracy or reliability of position measurements. It is also desirable that the material(s) of the sheath and other parts that may contact a patient's tissues be all of: biocompatible; not damaged by commonly available sterilization protocols; and able to withstand expected mechanical forces with a suitable safety margin as is appropriate for invasive medical equipment.

Nonmagnetic grades of stainless steel such as grade 304 stainless steel are available. However, even these grades tend to develop localized ferromagnetic properties when worked (as occurs, for example in making or modifying a stainless steel sheath or needle). This is a particular issue in applications in which it is desirable to deploy a position marker in an open-ended sheath or needle such that the cable or other assembly carrying the position marker must be sterile. In such cases it can be convenient to machine the tip of a stainless steel needle to serve as a biocompatible, sterile cover for a position marker and any associated cable. However, such machining can result in the stainless steel becoming magnetic in the vicinity of the machining operations.

In some embodiments a position marker is received within a stainless steel cover. The stainless steel cover is annealed after any machining operations and before use. Annealing involves heating the stainless steel to a high temperature (e.g. 1010° C. to 1120° C.) and then rapidly cooling the stainless steel. In addition to returning the stainless steel to a non-magnetic state, annealing the mechanical properties of the stainless steel. Annealed stainless steel tends to bend more easily than non-annealed stainless steel. The enhanced bendability of annealed stainless steel would normally be a severe disadvantage in the case of a needle to be introduced into the human body. Advantageously, however, in some embodiments of the invention the position marker and its cover are received within a sheath, such as a needle, which supports the cover and provides the desired mechanical stiffness which prevents the assembly from kinking or becoming undesirably bent in normal use. The sheath may, for example, comprise stainless steel in a hard state which has not been machined significantly and therefore does not require annealing to improve its magnetic properties.

Figure 9:
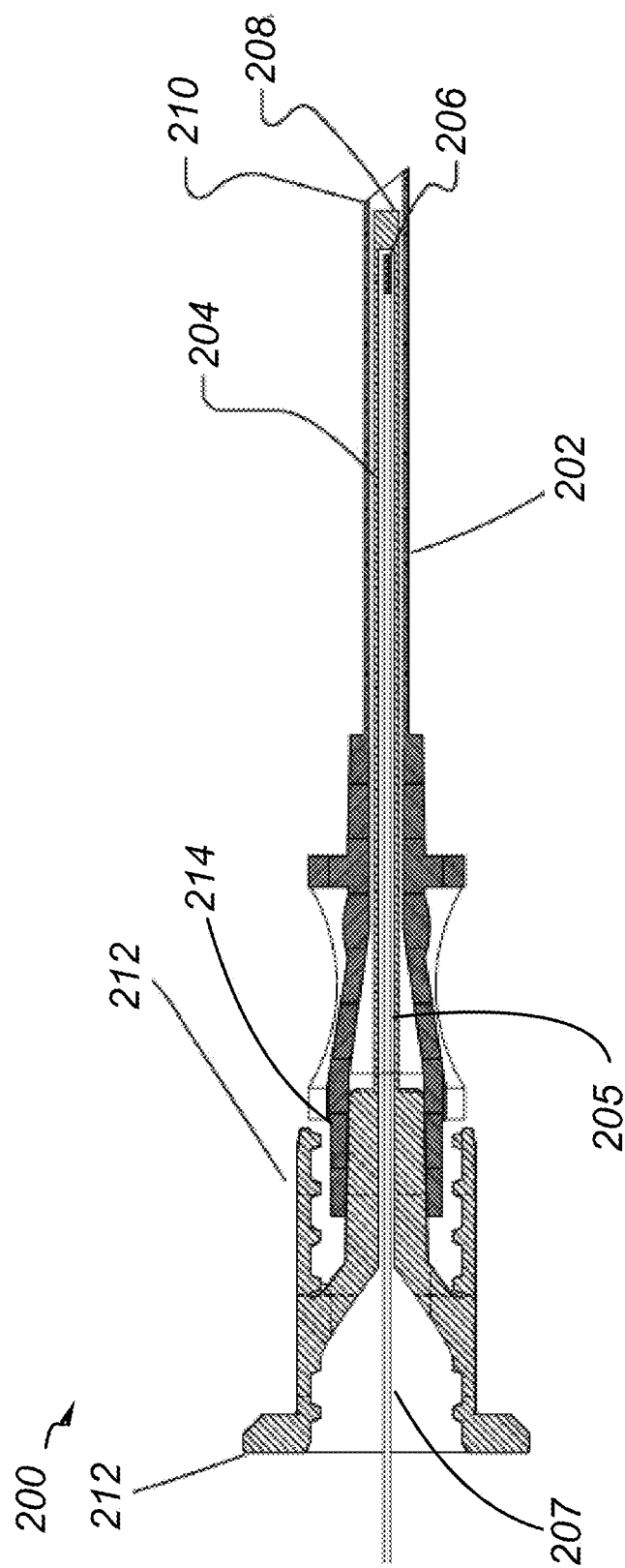
FIG. 9 is a cross section through a needle sheath assembly according to another example embodiment.

FIG. 9 illustrates a position-tracked instrument assembly 200 according to an alternative embodiment. Assembly 200 comprises a sheath 202 that receives a position sensor assembly 204 comprising a position marker 206. In the illustrated embodiment, sheath 202 may comprise stainless steel in a non-annealed state and position sensor assembly 204 may comprise a cover 205 of annealed stainless steel that encloses position marker 206 and signal carrier(s) 207 (which may comprise, e.g. wires, optical fibers or the like) connected to position marker 206.

In the illustrated embodiment, the end 210 of sheath 202 is open and the end 208 of position sensor assembly 204 lies just within the open end of sheath 202. Sheath 202 comprises a fitting 214 that engages a fitting 212 which is part of position sensor assembly 204. Fitting 214 may screw into threads on fitting 212, for example, by way of external threads (not shown in FIG. 9) on fitting 214.

Figures 10, 10A:
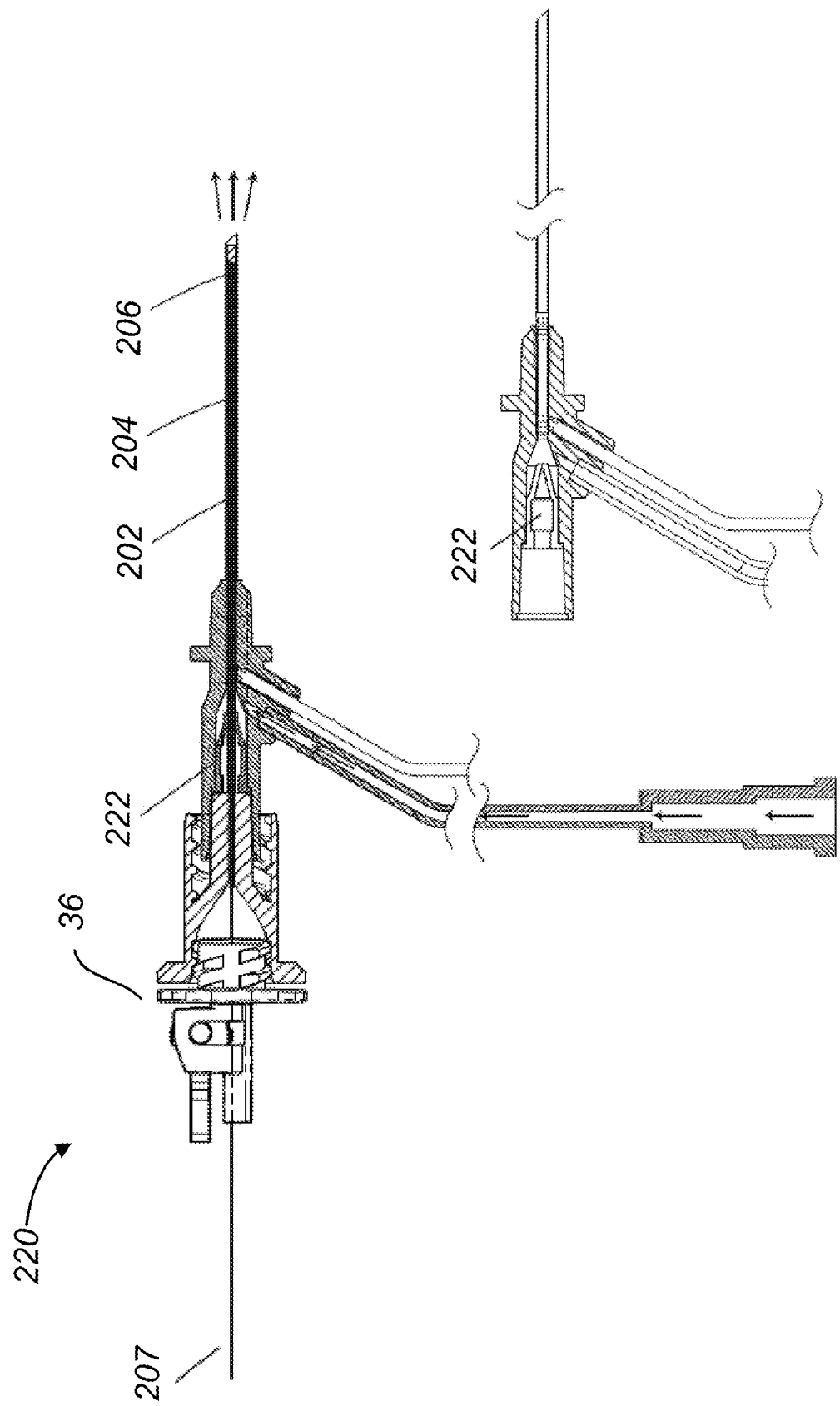
FIGS. 10 and 10A are cross sectional views through a needle sheath assembly with provision for the introduction of fluids according to another example embodiment.
Figure 11:
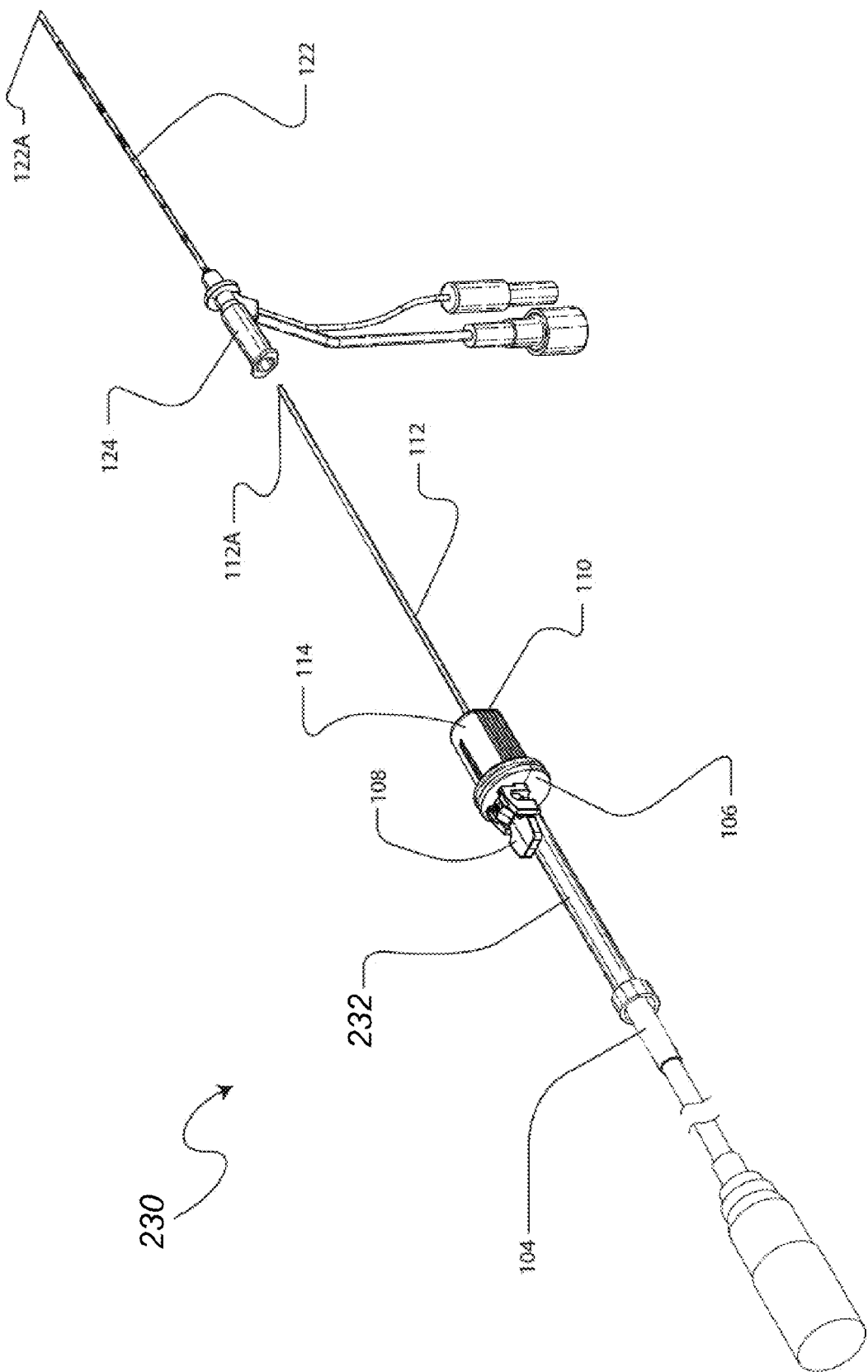
FIG. 11 is an isometric exploded view of a needle sheath assembly according to another example embodiment.

As shown in FIG. 10, in some embodiments, there is enough space for fluid to flow between position sensor assembly 204 and the interior of sheath 202. In such embodiments, fluid may be introduced into a patient while position sensor assembly 204 remains in place within sheath 202. FIG. 10 shows an assembly 220 in which fluid can be introduced through a fitting 221. The fluid can exit at the end of sheath 202. Assembly 220 includes a valve 222 through which position sensor assembly 204 can pass. Valve 222 seals around position sensor assembly 204 to prevent fluid introduced by way of fitting 221 from exiting through the fitting at the proximal end of sheath 202. Valve 222 may, for example, comprise a duckbill valve. FIG. 10A show valve 222 in a closed state with position sensor assembly 204 removed. In this configuration, FIG. 11 shows an assembly 230 according to another alternative embodiment. Assembly 230 is similar to assembly 100 shown in FIG. 8 with the addition of a sleeve 232 that limits how far position sensor 104 can be advanced into sheath 122.

FIG. 12 illustrates one way in which position sensor assembly 204 may be used in a sterile environment. Cover 205 is inserted through an aperture in a sterile flexible enclosure 240. Enclosure 240 may, for example comprise a sterile plastic sleeve. A sheath 202 (not shown in FIG. 12 may then be slid over cover 205. Enclosure 240 is then held between fitting 212 of position sensor assembly 204 and a corresponding fitting (not shown in FIG. 12) connected to sheath 202. Enclosure 240 prevents signal carrier(s) 207 from coming into contact with the environment outside of enclosure 240.

As will be apparent to those skilled in the art in the light of the foregoing disclosure, many alterations and modifications are possible in the practice of this invention without departing from the spirit or scope thereof. The embodiments described herein are only examples. For example, the above examples position a position marker near the tip of a member to be positioned, the position marker may be located adjacent another feature of the member. For instance, the position marker may be located adjacent a radial opening in a vacuum biopsy needle, fire biopsy needle, or the like. In some embodiments, one or more markings are provided on a sensor cable that, when the markings are aligned with a feature of a sheath and the sheath is installed in a member, result in a position marker affixed to the sensor cable being located adjacent a particular feature of the member. Other example embodiments may be obtained, without limitation, by combining features of the disclosed embodiments.

What is claimed is:

1. A medical apparatus comprising:
a position marker mounted on a cable, which includes a first end region and a second end region, wherein the position marker is secured to the second end region of the cable; and
a sheath, comprising:
a hub having a longitudinal aperture;
a tip;
a hollow shaft extending longitudinally from the hub to the tip, wherein the hollow shaft includes a lumen axially aligned with the aperture of the hub, the hollow shaft is dimensioned to receive the cable and the position marker, and the cable extends longitudinally in the hollow shaft from the hub to the tip with the first end region at the hub and the second end region at the tip; and
a connector base, including:
a transverse wall with a first side and a second side, wherein the transverse wall is transverse to the hollow shaft, the first side and the second side are opposing sides, and the first side is coupled to the hub;
a U-shaped elongate bracket having a long axis and projecting from the second side of the transverse wall, wherein the U-shaped bracket includes:
a bottom with a channel extending an entirety thereof along a first side of the bottom and in a direction of the long axis direction; and
opposing bracket walls projecting from opposing ends of the first side of the bottom and along the transverse wall; and
an attachment device coupled to the U-shaped elongate bracket and configured to secure the cable in the medical apparatus,
wherein the position marker indicates a position of the position marker by at least one of sensing a magnetic field or emitting an electromagnetic field, and the position of the position marker indicates the position of the tip of the sheath.

2. The apparatus according to claim 1, wherein the connector base further comprises a hollow channel projecting from the first side with a tapered end and a helical thread on an exterior surface, and the hub further comprises a complementary helical channel on an interior surface, and the helical thread is configured to engage the helical channel.

3. The apparatus according to claim 1, wherein the U-shaped elongate bracket includes a transverse aperture on each of the opposing walls, and the attachment device is pivotably coupled to the U-shaped elongate bracket at the transverse apertures and includes a cam configured for releasable locking frictional engagement with the cable.

4. The apparatus according to claim 2, further comprising:
a tubiform cover attached to the hub, the cover configured to extend from the hub to close over the tip and enclose the shaft in a first configuration.

5. The apparatus according to claim 4, wherein the cover comprises a flexible material, which can be drawn to transition the cover to a second configuration which inverts an outside surface to an inside surface and covers the cable extending from the hub opposite the tip.

6. The apparatus according to claim 2, wherein the cable comprises position-marking indicia spaced apart along the cable, the position-marking indicia alignable with a feature on the base for indicating a position of the position marker along the sheath relative to the end of the sheath.

7. The apparatus according to claim 1, further comprising:
a member projecting from the clamp, the member limiting a depth of insertion of the position marker into the sheath.

8. The apparatus according to claim 7, wherein the member comprises a plastic sleeve, the cable extends through the sleeve and an expanded portion on the cable limits the depth of insertion by contacting an end of the sleeve.

9. The apparatus according to claim 1 wherein the position marker comprises a magnetic position marker and the hollow shaft comprises a cover of an annealed austenitic stainless steel.

10. The apparatus according to claim 9, wherein the hollow shaft extends through a valve in the fitting into a hollow needle, the valve sealing around the hollow shaft to prevent egress of fluid by way of the fitting.

11. The apparatus according to claim 10, wherein the needle comprises an austenitic stainless steel in a non-annealed state.

12. The apparatus according to claim 11, wherein the hollow shaft and needle are configured to provide a fluid passage in a bore of the needle outside of the hollow shaft.

13. The apparatus according to claim 10, wherein the valve comprises a duckbill valve.

14. The apparatus according to claim 1, comprising a male fitting on a side of the hub adjacent to the hollow shaft, the male fitting concentric with the hollow shaft.

15. The apparatus according to claim 14, wherein the male fitting comprises a Luer fitting.

16. The apparatus according to claim 14 in combination with a needle comprising a female fitting connectible to the male fitting such that the hollow shaft extends into a bore of the needle, and the needle comprises a membrane disposed to seal around the hollow shaft.

17. The apparatus according to claim 1, wherein the position marker is configured to emit the electromagnetic field and further including:
   at least one non-imaging position sensor base unit configured to sense the emitted electromagnetic field and determine the position of the position marker.

18. The apparatus according to claim 1, further including:
   at least one non-imaging position sensor base unit configured to generate the magnetic field; and
   an ultrasound imaging system configured to illustrate the position of the hollow shaft on an image with the position of the position marker.

19. An elongate connector base for use with a position marker in guided instrument, the elongate connector base, including:
   a transverse wall with a first side and a second side, wherein the transverse wall is transverse to a long axis of the elongate connector; and
   a U-shaped bracket projecting out from the second side in a direction of the long axis of the elongate connector, where the U-shaped bracket includes:
      a bottom with an aperture and a first side, wherein the bottom projects out from the second side and the aperture is located opposite the transverse wall;
      opposing bracket walls projecting from different sides of the bottom and extending along the transverse wall with a space there between;
      a channel in the first side of the bottom between the opposing bracket walls and in the space and extending in the direction of the long axis of the elongate connector from the aperture to the transverse wall;
      an open top, and
      an open side, which opposes the transverse wall.

20. The connector base according to claim 19, further comprising:
   a hollow channel projecting from the first side in a direction opposing the U-shaped elongate bracket, wherein the hollow channel includes a tapered end and a helical thread on an exterior surface.

21. The connector base according to claim 20, further comprising:
   a transverse aperture on each of the opposing walls; and
   an attachment device pivotably coupled to the U-shaped elongate bracket at the transverse apertures; and
   a cam coupled to the U-shaped elongate bracket at the transverse apertures.

* * * * *